United States Patent
Wagner

(10) Patent No.: US 8,538,665 B2
(45) Date of Patent: Sep. 17, 2013

(54) CONTROL CIRCUIT FOR AN ELECTROCHEMICAL GAS SENSOR AND METHOD FOR ADJUSTING AN ELECTROCHEMICAL GAS SENSOR

(75) Inventor: Ekkehart-Peter Wagner, Bad Abbach (DE)

(73) Assignee: Continental Automotive GmbH, Hannover (DE)

( * ) Notice: Subject to any disclaimer, the term of this patent is extended or adjusted under 35 U.S.C. 154(b) by 286 days.

(21) Appl. No.: 12/989,449

(22) PCT Filed: Apr. 23, 2009

(86) PCT No.: PCT/EP2009/054864
§ 371 (c)(1),
(2), (4) Date: Dec. 23, 2010

(87) PCT Pub. No.: WO2009/130266
PCT Pub. Date: Oct. 29, 2009

(65) Prior Publication Data
US 2011/0093184 A1    Apr. 21, 2011

(30) Foreign Application Priority Data
Apr. 24, 2008   (DE) .......................... 10 2008 020 651

(51) Int. Cl.
*F02D 41/26*    (2006.01)
*G01M 15/10*   (2006.01)
*G06F 19/00*    (2011.01)

(52) U.S. Cl.
USPC ....... 701/109; 73/23.31; 73/114.73; 701/114; 204/401; 702/183

(58) Field of Classification Search
USPC ......... 701/102, 103, 109, 114, 115; 710/100, 710/305; 123/688, 690; 73/1.06, 31.05, 73/23.31, 23.32, 114.7–114.731; 204/401, 204/424–426; 702/182, 183, 185
See application file for complete search history.

(56) References Cited

U.S. PATENT DOCUMENTS

| | | | |
|---|---|---|---|
| 6,084,418 A | 7/2000 | Takami et al. | |
| 6,347,277 B2 | 2/2002 | Amtmann et al. | |
| 6,355,152 B1 * | 3/2002 | Kato et al. | 204/425 |
| 6,447,660 B2 | 9/2002 | Amtmann et al. | |
| 7,083,017 B2 * | 8/2006 | Hasuka et al. | 180/65.1 |
| 7,142,976 B2 * | 11/2006 | Inoue et al. | 701/114 |
| 7,164,976 B2 * | 1/2007 | Saeki et al. | 701/22 |
| 7,416,649 B2 | 8/2008 | Ieda et al. | |

(Continued)

FOREIGN PATENT DOCUMENTS

| | | |
|---|---|---|
| DE | 19708011 A1 | 9/1997 |
| DE | 19836127 A1 | 2/2000 |

(Continued)

*Primary Examiner* — Willis R Wolfe, Jr.
*Assistant Examiner* — Johnny Hoang
(74) *Attorney, Agent, or Firm* — Laurence A. Greenberg; Werner H. Stemer; Ralph E. Locher

(57) ABSTRACT

An electrochemical gas sensor is provided for a motor vehicle. The gas sensor contains a digital controller and a detection circuit. The digital controller captures, by a feedback input, a value of the voltage applied to the inside of the gas sensor cell. The output of the digital controller provides a control value for the current flowing in the gas sensor cell. The detection circuit is used to detect the properties of the gas sensor cell and to adjust the dynamic control properties of the digital controller corresponding to the properties of the gas sensor cell.

11 Claims, 2 Drawing Sheets

(56) References Cited

U.S. PATENT DOCUMENTS

| | | | |
|---|---|---|---|
| 8,097,146 B2 * | 1/2012 | Smith | 205/775 |
| 2004/0222094 A1 | 11/2004 | Ieda et al. | |
| 2005/0086998 A1 * | 4/2005 | Qin | 73/31.07 |
| 2006/0011476 A1 | 1/2006 | Hada et al. | |
| 2007/0129859 A1 * | 6/2007 | Saeki et al. | 701/22 |
| 2008/0053187 A1 | 3/2008 | Koring | |

FOREIGN PATENT DOCUMENTS

| | | |
|---|---|---|
| DE | 19836128 A1 | 2/2000 |
| DE | 102005033263 A1 | 2/2006 |
| DE | 102006030437 A1 | 1/2008 |
| DE | 102006041477 A1 | 3/2008 |
| DE | 102007043728 A1 | 4/2009 |
| EP | 1450418 A1 | 9/2004 |

* cited by examiner

CONTROL CIRCUIT FOR AN ELECTROCHEMICAL GAS SENSOR AND METHOD FOR ADJUSTING AN ELECTROCHEMICAL GAS SENSOR

BACKGROUND OF THE INVENTION

Field of the Invention

The invention relates to an electrochemical gas sensor and a method for adjusting an electrochemical gas sensor. Electrochemical gas sensors are used to measure concentrations of a predetermined gas component in a gas. In the case of internal combustion engines in motor vehicles for instance, the concentration of oxygen in the exhaust gas is measured. This measurement is used to determine whether the air/fuel ratio of the internal combustion engine has the desired value.

DE 10 2005 033 263 A1 proposes a gas concentration measuring device, with which the impedance of the gas sensor element is measured with the aid of a computation circuit for controlling activation and diagnosing the gas sensor element. To measure gas concentration the current flowing through the gas sensor or the voltage present across the gas sensor must be regulated. This serves to put the gas sensor in a state in which the concentration can be measured.

It has proven that gas sensors are subject to major production variations, so that their electrical properties, such as impedance, differ by up to 20% for instance from gas sensor to gas sensor. To ensure that the control circuit does not become unstable even when there are major deviations, the controller must be designed so that it responds relatively slowly. This means that the air/fuel ratio is not stable all the time, resulting in the unnecessary consumption of a large quantity of fuel.

BRIEF SUMMARY OF THE INVENTION

The object of the invention is therefore to provide an electrochemical gas sensor that can be controlled more quickly.

It is also the object of the invention to provide a method for adjusting such an electrochemical gas sensor.

These objects are achieved by the subject matter of the independent claim. Further advantageous embodiments will emerge from the subclaims.

The invention relates to a control circuit for an electrochemical gas sensor for a motor vehicle, with which a digital controller is provided, featuring a feedback input and an output. The digital controller receives a value for the voltage present across a gas sensor cell by way of the feedback input. At the output the digital controller supplies a control value for a current flowing into the gas sensor cell.

A detection circuit is provided for detecting the properties of the gas sensor cell. It is also provided for adjusting the dynamic control properties of the digital controller according to the properties of the gas sensor cell.

The dynamic control properties of the digital controller are characterized for example by a z-transformed $$F_z(z) = \frac{a_1 z + a_2}{z^2 + b_1 z + b_2}.$$

During adjustment the parameters $a_1$, $a_2$, $b_1$ and $b_2$ are changed. The dynamic properties of the digital controller characterize how quickly and in some instances the overshoots with which the digital controller responds to deviations in the setpoint value.

The electrochemical gas sensor has the advantage that the digital controller can be adjusted according to the properties of the gas sensor cells. It is thus possible to tailor the controller property in each instance to the installed gas sensor cell, with the result that the digital control circuit is adjusted so that it responds quickly when there are deviations, without endangering the stability of the control loop.

The control parameters can also be tailored to the operating state of the gas sensor and temperature. It is also possible to use sensors of different types, for instance from different manufacturers, as the digital controller with the detection circuit can be tailored automatically.

In one embodiment the detection circuit is provided at least partially in a microcontroller. The microcontroller can manage a plurality of data, which is compared with the detected properties of the gas sensor cell.

The detection circuit is preferably configured so that it detects the properties of the gas sensor cell based on the voltage occurring across the gas sensor cell, when a current step is present at the output of the digital controller. Step responses are characteristic of the dynamic behavior of control elements and thus allow ready conclusions to be drawn about the control properties of the measured gas sensor cell.

In a further embodiment the detection circuit is also configured to detect the temperature of the gas sensor cell. Temperature is also a major influence on the behavior of the gas sensor cell. It is therefore helpful to consider the properties of the gas sensor cell at the measured temperature, to draw a conclusion about the sensor type for instance.

In a further embodiment the property of the gas sensor cell is calculated based on the impedance of the gas sensor cell, in order to characterize the gas sensor cell as accurately as possible.

In a preferred embodiment the detection circuit features an analog/digital converter for converting the voltage present across the gas sensor cell. Conversion to a digital value allows the digital calculation of gas sensor properties, which simplifies the comparison with already known gas sensors.

It is particularly appropriate to employ the described electrochemical gas sensor, if the gas sensor cell contains a Nernst cell, since such a cell is produced by a plurality of manufacturers, in each instance with major production variations.

The invention also relates to the use of an inventive electrochemical gas sensor in a motor vehicle to control the air/fuel mixture of an engine of the motor vehicle. The inventive provision of the detection circuit allows more precise adjustment of the control circuit for the gas sensor. This allows the electrochemical gas sensor to be controlled more dynamically, making it faster, which ultimately reduces fuel consumption.

The invention also relates to a method for adjusting an electrochemical gas sensor, with an inventive control circuit first being provided for an electrochemical gas sensor. The output of the digital controller is controlled so that the current at the output generates a step of maximum gradient. The properties of the gas sensor cell are then detected based on the voltage at the feedback input of the digital controller. This method can be used to characterize the gas sensor cell, in order to adjust the properties of the digital controller as a function of the properties of the gas sensor cell.

In one preferred embodiment the method is used to check the exhaust gas flow of an engine and the steps of activating the output and detecting the properties of the gas sensor cell are performed at least when the engine is started up. It is thus checked every time the engine is started up, whether the properties of the gas sensor cell have changed, for example due to aging, or whether a new gas sensor cell has been fitted during a repair. The digital controller is then tailored to the changed properties of the gas sensor cell.

In a further embodiment the control properties are adjusted a number of times during the trip, to tailor them to any temperature changes.

DESCRIPTION OF THE INVENTION

Figure 1:
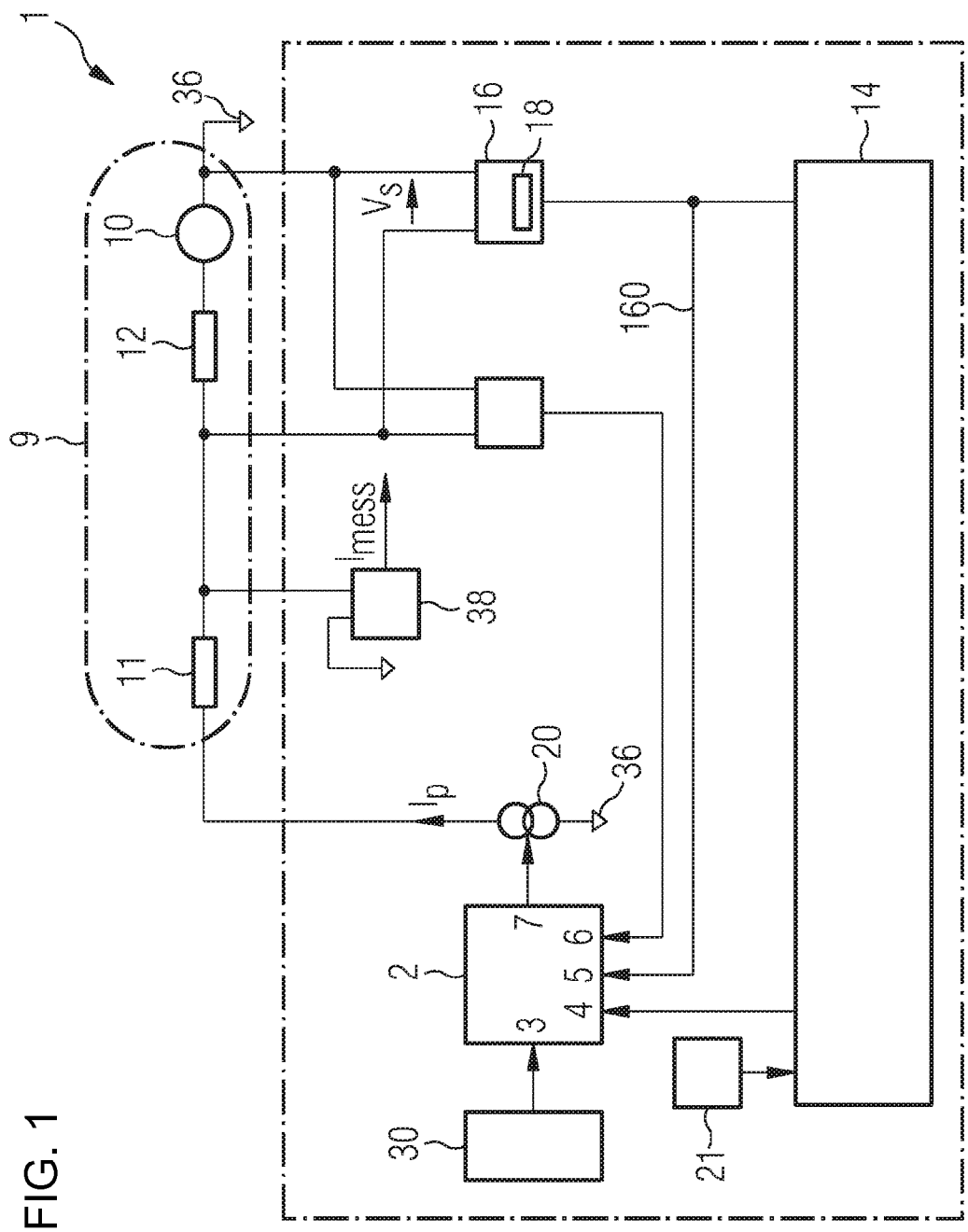
FIG. 1 shows an inventive control circuit for a gas concentration sensor.

FIG. 1 shows an inventive control circuit for electrochemical gas concentration sensors. The assembly 1 consisting of a control circuit 100 and a Nernst cell 9 contains a Nernst cell 9, as well as a digital controller 2 and a setpoint value generator 30. The digital controller 2 controls a current source 20, which determines the current Ip flowing into the Nernst cell 9. The digital controller receives a setpoint value for controlling the current regulator 20 at its first input 3. All the elements in FIG. 1, which are not part of the Nernst cell 9, are part of the control circuit 100.

The Nernst cell 9 contains a first resistor 11, which represents the resistance across the supply lines to the Nernst cell, and a second resistor 12, which represents the internal resistance of the Nernst cell 12. A voltage 10 drops across the Nernst cell 9, being identified by the circle. The first resistor 11, the second resistor 12 and the voltage 10 are connected to one another in series. The first connection of the voltage 10 is connected to ground 36 here, while its second connection is connected to a first connection of the second resistor 12.

The second connection of the second resistor 12 is connected to the first connection of the first resistor 11, the second output of which is connected to the output of the current source 20. The first input of the sampling element 16 is connected to ground 36 and its second input is connected to the second connection of the second resistor 12. The voltage Vs is generated between these two inputs of the sampling element 16 and then converted to a digital value in said sampling element. This digital value is fed to the input 5 of the digital controller 2 by way of the feedback path 160.

The proposed gas sensor is a lambda control oxygen sensor. It ensures that the engine is operated with a constant air/fuel mixture. The voltage Vs is adjusted to a constant value. The digital controller 2 controls the current source 20 at its output 7 so that the current Ip brings about a voltage Vs, which is equal to the voltage in the setpoint value generator 30. The size of the current Ip is a measure of the lambda value.

The voltage Vs is also measured by the limiter 17. This limiter 17 measures whether the voltage Vs exceeds a specified threshold value. If so, the limiter 17 outputs a signal value to the digital controller 2, which receives this value at its input 6. If the voltage Vs exceeds the previously specified threshold value, the current Ip is reduced.

The current Ip is measured using a measurement circuit identified with the reference character 38 in the figure. The measured value Imess is a measure of the lambda value to be set in the engine controller and is output to the microcontroller of the engine controller.

The microprocessor 14 contains a detection circuit for identifying the properties of the Nernst cell 9. When the engine starts up, the digital controller 2 controls the current source 20 so that it performs a current step from 0 mA for example to 5 mA. The driver of the current source 20 is dimensioned so that the rise is as steep as possible. The profile of the voltage Vs responds correspondingly to this current step. As described above, the voltage Vs is sampled by the sampling element 16 and converted to digital values using the AD converter 18 present in the sampling element. The sequence of digital values is output to the detection circuit 14. The detection circuit 14 identifies properties of the Nernst cell 9 from the voltage profile Vs.

Nernst cells 9 from different manufacturers and different production batches differ in their transmission behavior. The measured step response characterizes the transmission behavior of the Nernst cell 9 and is used as the basis for control evaluation. The frequency profiles of different types of Nernst cells are stored in the storage unit 21. The detection circuit 14 compares the voltage profiles received from the sampler 16 with the voltage profiles stored in the storage unit 21.

Once the detection circuit 14 has identified the correct sensor type, it adjusts the properties of the digital controller 2. To this end it changes the transmission characteristic of the digital controller 2. The digital transmission characteristic of the digital controller 2 is characterized by amount and phase by a Bode diagram for example. The characteristics are adjusted by means of an amount/phase calibration according to the properties of the Nernst cell.

Sensors are generally manufactured with significant production variations. Deviations of up to 20% in transmission behavior are not uncommon. The detection circuit 14 can be used to detect whether such deviations from a normal value are present. If so, the digital controller 2 is also adjusted so that the control behavior of the system as a whole is optimized.

The use of the digital control structure in particular allows the necessary adaptations of the control parameters to be extracted directly from the step response of the sensor by means of software. The changed control parameters can be programmed directly into the digital controller 2. The filter structure has the advantage that the control characteristic can be tailored easily to different states of the connected linear lambda probe. If a different type of probe is connected, it is only necessary to change the data in the detection circuit 14, which is much easier and quicker than a hardware change.

If the detection circuit 14 is programmed so that it can also evaluate parameters such as trim resistance, heating resistances and the step response of the probe, it is also possible to tailor the control characteristic in a fully automatic manner to different predefined sensor types or even to tailor the controller characteristic individually in a fully automatic manner to the attached sensor.

The fully automatic calibration of the controller characteristic allows intelligent differentiation between different types of linear lambda sensors and automatic adaptation of the control circuit.

The controller characteristic is tailored individually to the respective connected linear lambda sensor in order to tailor control behavior taking into account the frequency characteristic of the sensor due to production variance, aging and temperature fluctuations for instance.

Figure 2:
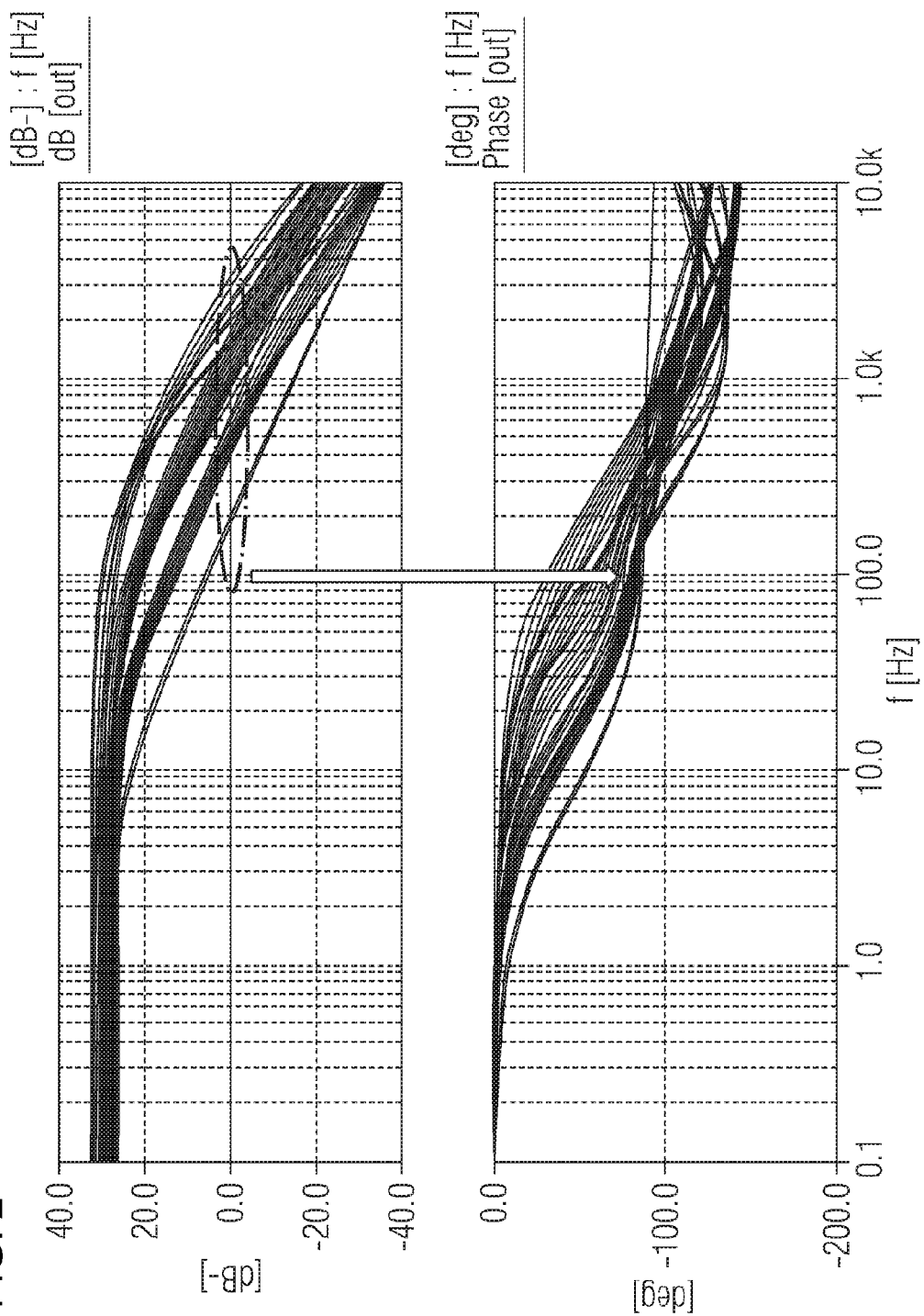
FIG. 2 shows the frequency behavior of an inventive gas compensation sensor.

FIG. 2 shows a Bode diagram of the control characteristic of an open control circuit of a gas sensor according to FIG. 1. A plurality of simulations have been carried out, in which the properties of the digital controller 2 and the gas sensor 9 were varied according to their production deviations. It has proven that the amplitude and frequency profiles of the open control circuit are very dependent on the parameters of the digital controller 2 and the gas sensor 9.

The phase reserve at amplification 0 dB is read off to assess the stability of the control circuit. The phase reserve varies between 60 and 100° in the simulations shown in FIG. 2. In order to be able to increase the phase reserve, the properties of the digital controller 2 are made dependent on the properties of the gas sensor 9. This reduces the variation in the amplitude and frequency profiles of the Bode diagram. This allows a higher value to be achieved for the phase reserve.

The invention claimed is:

1. A control circuit for an electrochemical gas sensor for a motor vehicle, the control circuit comprising:
   a digital controller having a feedback input and an output, said digital controller receiving a value for a voltage present across a gas sensor cell by way of said feedback input, said output supplying a control value for a current flowing into the gas sensor cell; and
   a detection circuit for detecting properties of the gas sensor cell and for adjusting dynamic control properties of said digital controller according to the properties of the gas sensor cell;
   wherein said detection circuit detects the properties of the gas sensor cell based on the voltage dropping across the gas sensor cell when a step is applied to the current flowing into the gas sensor cell.

2. The control circuit for the electrochemical gas sensor according to claim 1, wherein said detection circuit is provided at least partially in a microcontroller.

3. The control circuit for the electrochemical gas sensor according to claim 1, wherein said detection circuit calculates the properties of the gas sensor cell based on a step response of the gas sensor cell.

4. The control circuit for the electrochemical gas sensor according to claim 1, wherein said detection circuit calculates the properties of the gas sensor cell based on an impedance of the gas sensor cell.

5. The control circuit for the electrochemical gas sensor according to claim 1, further comprising an analog/digital converter for converting the voltage present across the gas sensor cell, said analog/digital converter connected to said detection circuit.

6. The control circuit for the electrochemical gas sensor according to claim 1, further comprising a storage unit having a data record for properties of gas sensor cells and connected to said detection circuit.

7. The control circuit for the electrochemical gas sensor according to claim 1, further comprising an analog/digital converter for converting the voltage across the gas sensor cell to a digital signal, said analog/digital converter connected to said detection circuit.

8. An assembly, comprising:
   a gas sensor cell for analyzing an exhaust gas; and
   a control circuit for said gas sensor cell, said control circuit containing:
      a digital controller having a feedback input and an output, said digital controller receiving a value for a voltage present across said gas sensor cell by way of said feedback input, said output supplying a control value for a current flowing into said gas sensor cell; and
      a detection circuit for detecting properties of said gas sensor cell and for adjusting dynamic control properties of said digital controller according to the properties of said gas sensor cell;
      wherein said detection circuit detects the properties of the gas sensor cell based on the voltage dropping across the gas sensor cell when a step is applied to the current flowing into the gas sensor cell.

9. A control method, which comprises the steps of:
   providing a control circuit for an electrochemical gas sensor for a motor vehicle, the control circuit containing a digital controller having a feedback input and an output, the digital controller receiving a value for a voltage present across a gas sensor cell by way of the feedback input and the output supplying a control value for a current flowing into the gas sensor cell, the control circuit further having a detection circuit for detecting properties of the gas sensor cell based on the voltage present across the gas sensor cell when a step is applied to the current flowing into the gas sensor cell and for adjusting dynamic control properties of the digital controller according to the properties of the gas sensor cell; and
   controlling, via the control circuit, an air/fuel mixture for an engine of the motor vehicle.

10. A method for adjusting an electrochemical gas sensor, which comprises the steps of:
   supplying a gas sensor cell for a motor vehicle;
   supplying a control circuit for the gas sensor, the control circuit containing a digital controller having a feedback input and an output, the digital controller receiving a value for a voltage present across the gas sensor cell by way of the feedback input and the output supplying a control value for a current flowing into the gas sensor cell, the control circuit further having a detection circuit for detecting properties of the gas sensor cell based on the voltage present across the gas sensor cell when a step is applied to the current flowing into the gas sensor cell and for adjusting dynamic control properties of the digital controller according to the properties of the gas sensor cell; and
   controlling the output of the digital controller so that the current flowing into the gas sensor cell has a current step;
   detecting the properties of the gas sensor cell based on the voltage present across the gas sensor cell when the step is applied to the current flowing into the gas sensor cell; and
   adjusting the dynamic control properties of the digital controller.

11. The method according to claim 10, which further comprises:
   checking an exhaust gas flow of an engine of the motor vehicle; and
   performing the controlling and detecting step at least when the engine is started up.

* * * * *